United States Patent

Dokken

[11] Patent Number: 5,368,585
[45] Date of Patent: Nov. 29, 1994

[54] REUSABLE DIAPER AND COVER COMBINATION

[76] Inventor: Glenda K. Dokken, 6921 Dundee St., Corpus Christi, Tex. 78413

[21] Appl. No.: 864,536

[22] Filed: Apr. 7, 1992

[51] Int. Cl.⁵ .............................................. A61F 13/15
[52] U.S. Cl. .................................. 604/393; 604/391; 604/385.1; 604/358
[58] Field of Search ............... 604/385.2, 391, 393, 604/394, 397, 398, 385.1, 358

[56] References Cited

U.S. PATENT DOCUMENTS

| | | | |
|---|---|---|---|
| 2,493,113 | 1/1950 | Dance | 604/394 |
| 2,545,761 | 3/1951 | Brink | 604/394 |
| 2,577,398 | 12/1951 | Blake | 604/398 |
| 2,638,899 | 5/1953 | Ambasian | 604/397 |
| 2,890,701 | 6/1959 | Weinman | 604/394 |
| 2,893,393 | 7/1959 | Pressley | 604/394 |
| 3,039,466 | 6/1962 | Wilson | 604/398 |
| 4,051,854 | 10/1977 | Aaron | 604/394 |
| 4,597,761 | 7/1986 | Buell | 604/397 |
| 4,906,243 | 3/1990 | Drarland | 604/394 |
| 4,955,880 | 9/1990 | Rodriguez | 604/393 |
| 5,019,067 | 5/1991 | Simmons | 604/385.2 |
| 5,069,672 | 12/1991 | Wippler et al. | 604/398 |
| 5,087,255 | 2/1992 | Sims | 604/385.2 |
| 5,108,385 | 4/1992 | Snyder | 604/397 |
| 5,112,326 | 5/1992 | Quadrini | 604/391 |
| 5,137,526 | 8/1992 | Coates | 604/398 |

FOREIGN PATENT DOCUMENTS

| | | | |
|---|---|---|---|
| 9008524 | 8/1990 | WIPO | 604/393 |
| 9203999 | 3/1992 | WIPO | 604/394 |

Primary Examiner—Randall L. Green
Assistant Examiner—Rob Clarke
Attorney, Agent, or Firm—Donald R. Comuzzi; Christopher L. Makay

[57] ABSTRACT

A diaper set consisting of a gas permeable, water impervious outer cover and a water absorbent reusable pad. The pad and cover have mating hook and loop fasteners to secure the pad to the cover. The cover has fastening means for connecting the cover around the waist of the wearer.

6 Claims, 4 Drawing Sheets

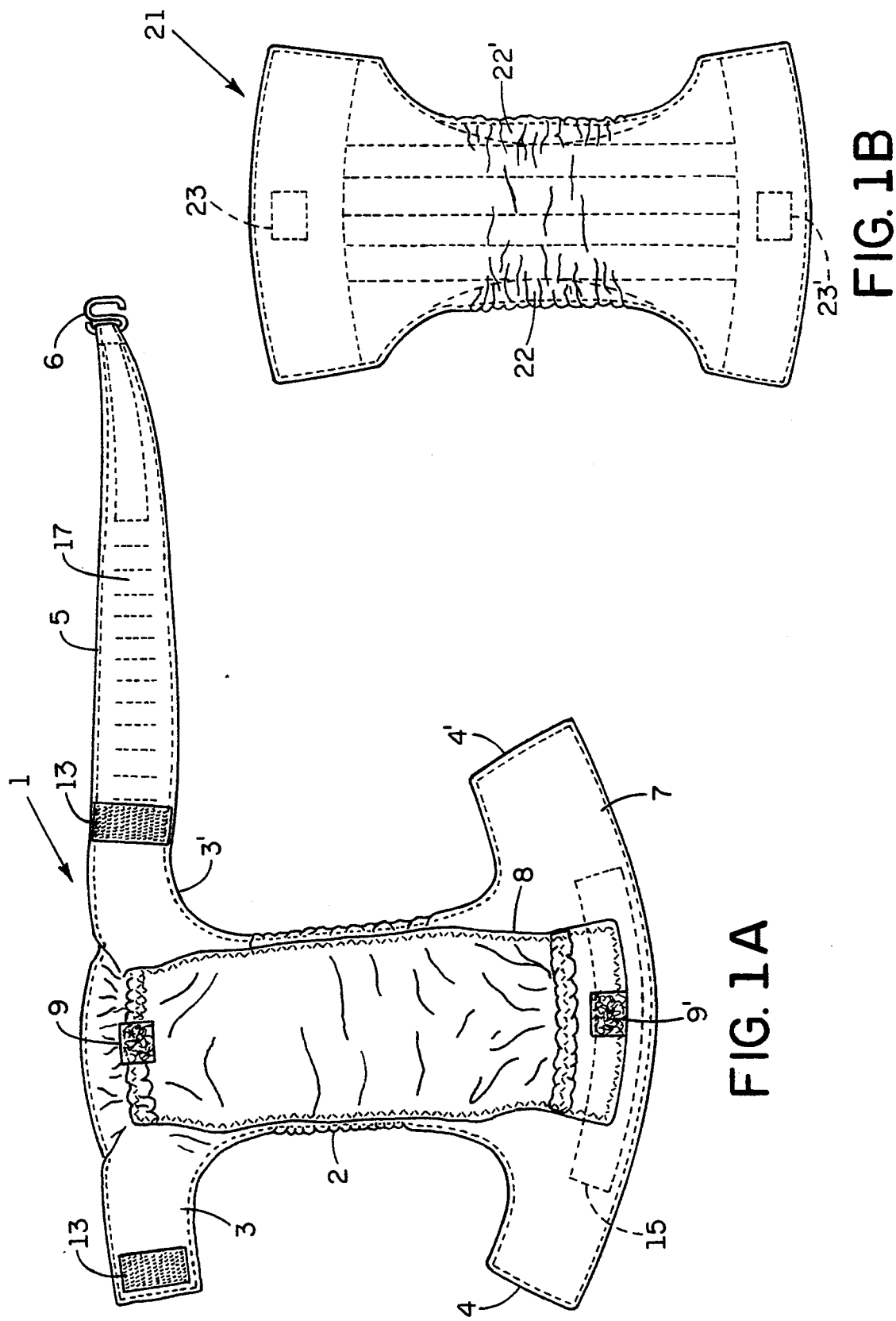

REUSABLE DIAPER AND COVER COMBINATION

BACKGROUND OF THE INVENTION

The present invention relates to a novel diaper and cover combination for use in diapering young children and incontinent adults. More specifically, it relates to a reusable diaper and cover combination made of a washable material which can be integrated into a substantially unitary garment when placed on the user.

Diaper and cover combinations are fairly common for use with disposable diapers and either reusable or disposable covers. Covers and regular rectangular cotton diapers are also commonly used.

The novel aspects of the present invention relates to the relationship of the diaper to the cover which forms an essentially unitary garment, that is easy to use and which can be washed and reused.

Today, we are all very aware of the environment and the pressure that is placed on it by the so called "convenience" items both food and clothing. Increased use of disposable clothing and particularly diapers have given rise to great concern by many ecologists. This creates an enormous disposal and sanitation problem.

It is an object of the present invention to eliminate the problem caused by disposable diapers but retain the convenience and ease associated with their use.

It is also an object of the present invention to provide a garment that is both comfortable and pleasing in appearance and is easy to use.

SUMMARY OF THE INVENTION

My invention relates to a two-piece diaper cover and reusable diaper combination that is easy to use, pleasing in appearance, and comfortable to the wearer. It consists of an outer cover having an outer surface made of cotton or other natural fiber fabrics and an inner surface made of a moisture impervious material and a diaper made of cotton and contoured to fit both the wearer as well as the outer cover.

Several attempts to address the aforementioned problems are disclosed in the prior art. U.S. Pat. No. 4,872,871 discloses a unitary disposable diaper and cover which look like a two-piece design.

U.S. Pat. No. 4,596,568 discloses a two part design for an outer cover with means for fastening a rectangular cotton diaper thereto.

U.S. Pat. No. 3,882,871 discloses a diaper cover with means for attaching a disposable diaper pad therein.

The primary purpose of the present invention is to provide a reusable diaper and cover that is easy to install, is comfortable to the wearer and is pleasing in appearance. Of course, the product must posses the other inherent characteristics such as a gas permeable outer cover that is impervious to moisture and has sufficient stretchability as not to hamper the mobility of the wearer. The inner diaper pad must be moisture absorbent and soft enough as not to irritate the skin. Preferably the diaper is made of layers of cotton fabric such as cotton pique, cotton flannel and/or cotton terry. A layer of polyvinyl material is interposed between the cotton layers in the pocket formed adjacent the padded portion in the crotch of the diaper. The several layers are fastened as by stitching into a unitary diaper. Furthermore, the diaper is contoured to fit the wearer as well as to match perfectly with the shape of the outer cover. It has suitable fasteners to connect it to fasteners on the cover. The outer cover is made of a suitable breathable material which will permit air circulation but retain moisture. A polyvinyl fabric marketed under the trademark "ULTREX" is such a material. The outer cover is a single contoured design that has an "I" shape configuration to wrap around the back of the wearer's mid-section and to extend up between the legs and extend around the front of the mid-section. Suitable fastening means are provided to fasten the cover in place around the mid-section. Additional fastening means are provided on the inside of the cover for connecting the fitted diaper thereto.

BRIEF DESCRIPTION OF THE DRAWINGS

FIG. 1A is a plan view of the diaper cover.

Fig. 1B is a plan view of the contoured, fitted diaper.

DESCRIPTION OF THE PREFERRED EMBODIMENT

Figure 2A:
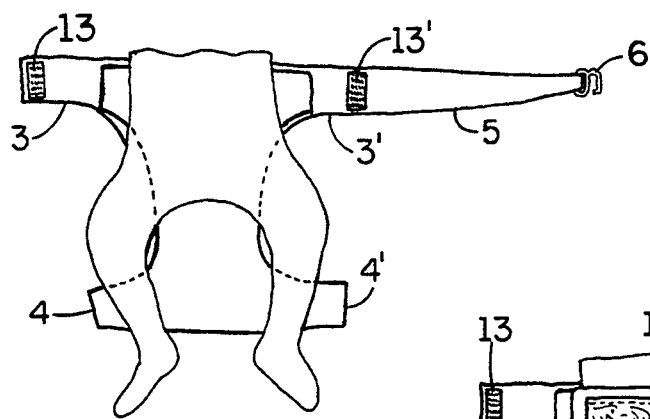
FIGS. 2A–2E depicts the diaper and cover being positioned on a child.
Figure 2B:
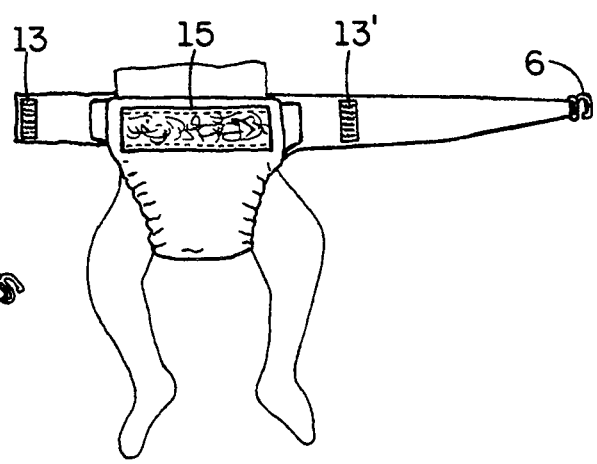
Figure 2C:
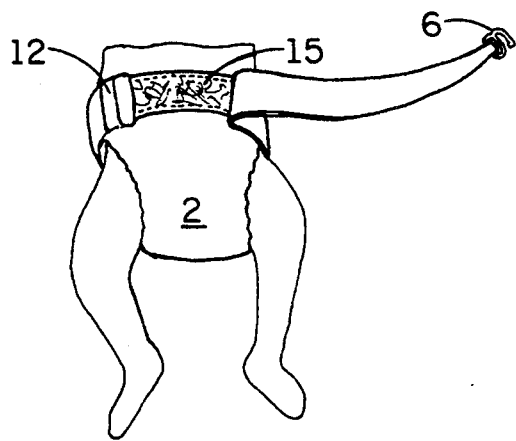
Figure 2D:
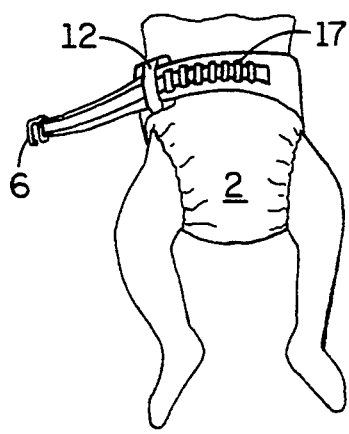
Figure 2E:
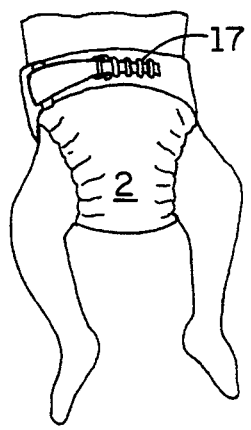

Referring now to the drawings, a diaper set according to the invention comprises a diaper cover 1 depicted in FIG. 1A and a contoured diaper pad 21 depicted in FIG. 1B. The diaper cover 1 consists of a central portion 2 for covering the buttocks and genitals and top wing portion 3 and 3' for encircling the waist and bottom wing portions 4 and 4' for encircling the back and a belt loop 12 is stitched to the outside of wing portion 3 (see FIG. 2D). The top wing portion 3' has an extended belt portion 5 with stitched loop 17 on the outside and a hook 6 at the end thereof for wrapping across the front of the waist in the manner shown in FIGS. 2A–2D for fastening as shown in FIG. 2E.

The cover has outer and inner surfaces, the outer surface faces away from the wearer's body and the inner surface faces the wearer's body and is made up of a plurality of layers of material, the outer layer 7 is made from a suitable fabric such as cotton for appearance and which is also washable and an inner layer 8 of a suitable fabric that is air permeable but which is impervious to moisture. This inner layer may be made of a suitable fabric possessing these quantities such as a polyvinyl sold under the trademark "ULTREX". This inner layer covers virtually the entire inside surface of the cover except where the cover might touch the wearer's body. It is very important that only cotton touch the wearer's body. The layers of materials are fastened together as by stitching or by a suitable adhesive. The edges may be gathered in a manner to produce a ruffled appearance.

The diaper pad 21 is made of multiple layers of washable materials, preferably cotton or a combination of cotton and cotton or polyester batting interposed between the cotton layers. The various layers are connected by sewing or a suitable adhesive. The diaper pad is contoured to fit the contour of the outer cover, both of which are contoured to fit the wearer's body. On either side of the crotch portion of the diaper pad, pockets 22, 22' are provided and a piece of polyvinyl material is inserted in the pocket. This acts to further retain moisture from leaking around the area adjacent the wearer's leg.

Hook and loop fasteners are the preferred means for fastening the diaper pad 21 to the diaper cover 1. Loop fasteners 9 and 9' are mounted on the inside surface of the top and bottom of the central portion 2 between the upper wing portions 3, 3' and lower wing portions 4, 4'.

Hook fasteners 23, 23' are mounted on the outside of the diaper pad 21 for engaging the loop fasteners 9, 9' to fasten the diaper pad 21 to the outer cover 1.

Hook fasteners 13 and 13' are mounted on the inside of the top wing portions 3, 3'. A strip of loop fastener 15 is mounted on the outside of the bottom end of central portion 2.

The diaper pad 21 is first positioned on the outer cover 1 and attached thereto by means of hook and loop fasteners as described above. The diaper set consisting of the cover and pad is then positioned underneath the wearer. The cover with diaper pad attached is pulled up the back and front of the wearer so that the central portion 2 of the cover is covering the buttocks and genitals. The belt portion 5 is wrapped across the stomach and through the belt loop 12. The belt portion is then pulled back across the loop and over the stomach in the opposition direction and the hook 6 is fastened in one of the stitched loops 17.

When the upper wing portion 3, 3' are wrapped across the stomach of the wearer, the hooks fasteners 13, 13' engage the loop fastener strip 15 and is connected thereto.

Figure 3A:
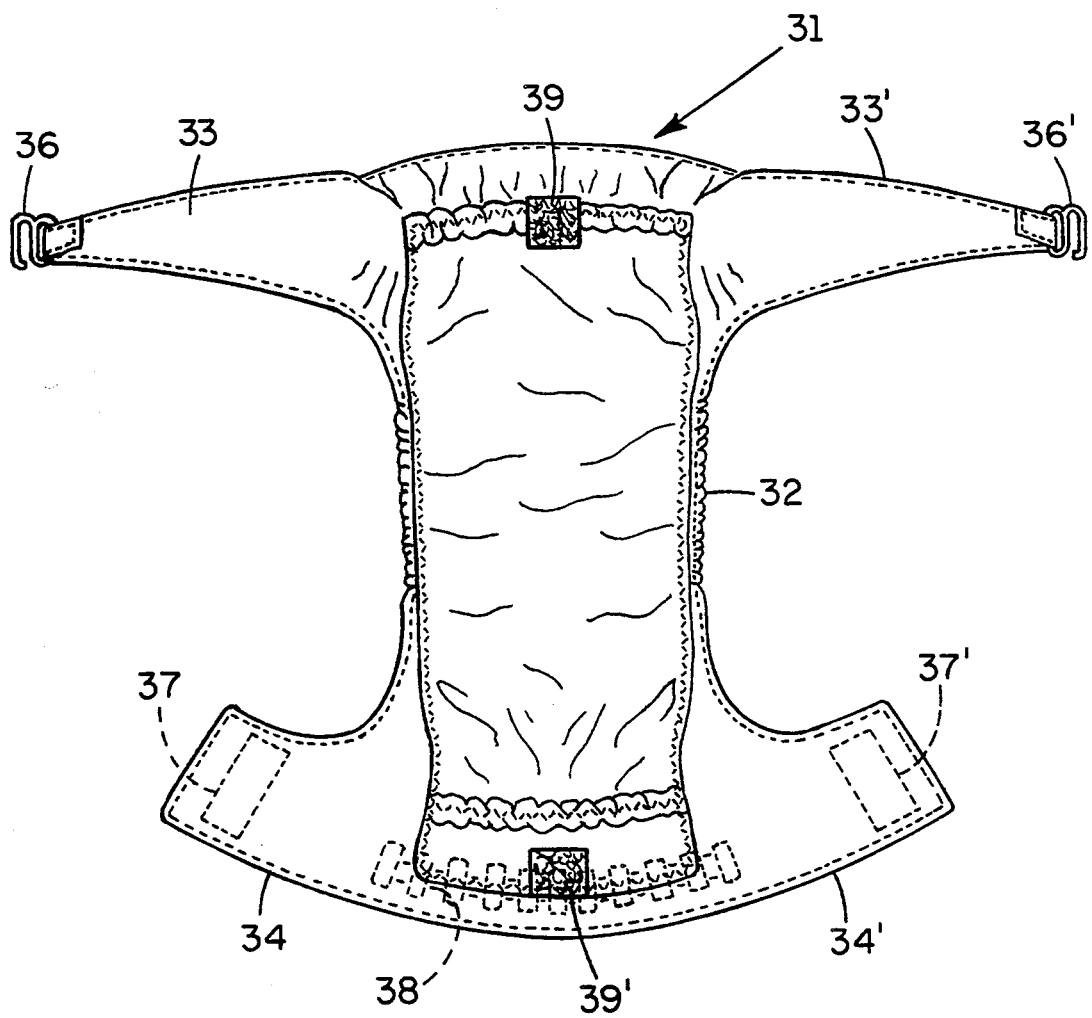
FIG. 3A is a plan view of an alternative embodiment of the diaper cover.

FIG. 3A shows an alternative diaper cover 31 which is very similar in construction to the cover 1 depicted in FIG. 1A except that the belt portion has been eliminated. The various components of the cover 31 performs the same function as like components of the cover 1. The cover is also constructed from the same type fabrics.

Figure 3B:
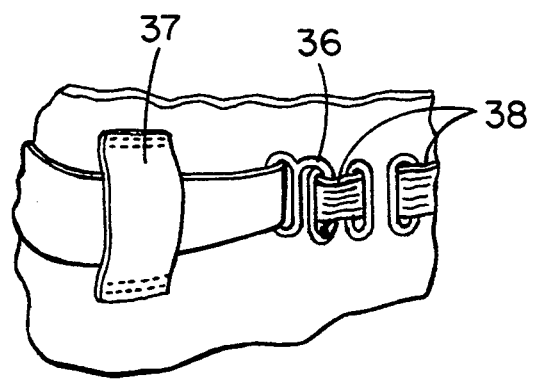
FIG. 3B is a detail view of the fastening means of FIG. 3A.

The diaper cover 31 has a central portion 32, top wing portions 33, 33' and bottom wing portions 34, 34'. The top wing portions extend outwardly from the central portion and have a hook 36, 36' attached at each end thereof. Belt loops 37, 37' are mounted on the outside end of the lower wings 34, 34'. Loops 38 are mounted on the outside of the bottom end of the central portion 32. The fitted diaper pad 21 is attached to the cover 31 in the same manner as described with reference to cover 1. With the pad attached by fastening hooks 23, 23' to loops 39, 39', the combination diaper set is positioned on the wearer as previously described. With the lower wings 34, 34' positioned over the waist of the wearer, the upper wing portions 33, 33' are inserted through the belt loops 37, 37' respectively and the hooks 36 and 36' are attached to the loops 38 as shown in FIG. 3B. As is readily apparent, while FIG. 3B only depicts the details of the left side wing portion 33 being attached, right side wing portion 33' is attached in like manner.

Figure 4:
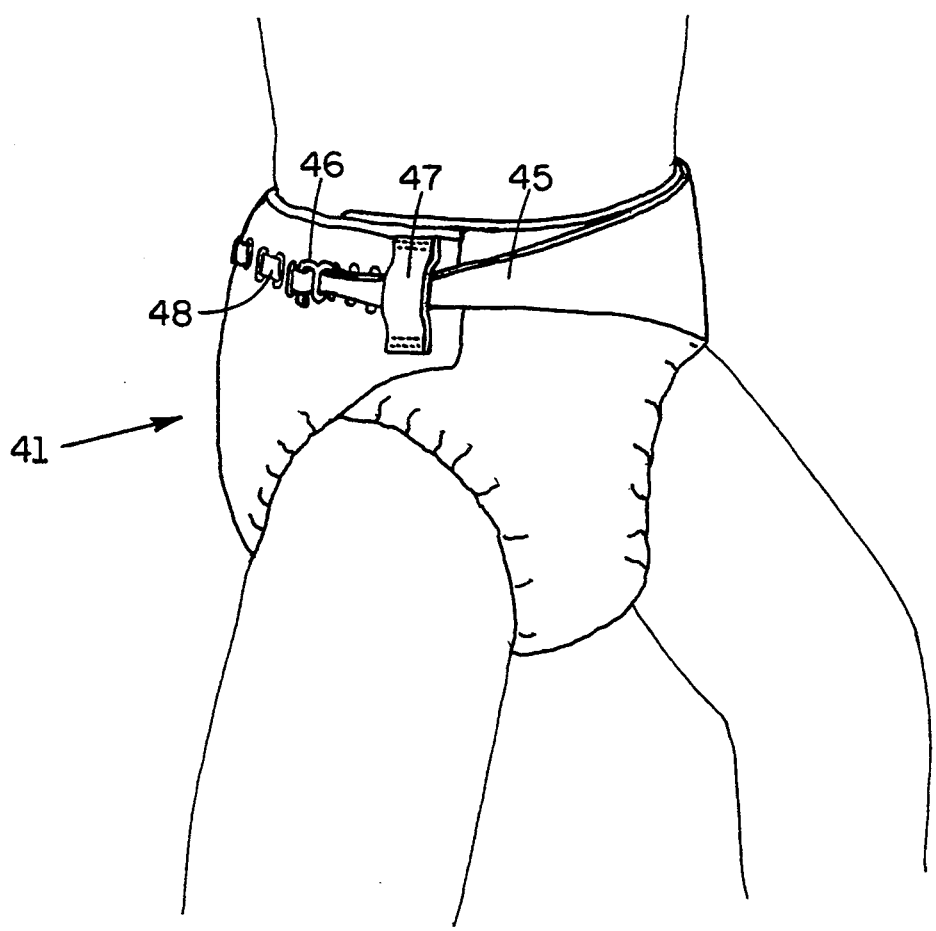
FIG. 4 is a perspective view of a diaper cover similar to FIG. 1 depicting a modified fastener means.

FIG. 4 depicts another means of fastening the diaper cover around the wearer. The cover with attached diaper pad is positioned on the wearer in the manner previously described. The outer cover which is shown generally as 41 has two bottom wings portions which are positioned around the waist of the wearer from front to back. The upper wing portions are positioned in overlapping relationship to the lower wing portion from back to front. One wing portion has a belt portion 45 which extends across the front of the wearer and through a belt loop 47 mounted on the outside of the other wing portion. A hook 46 is attached at the end of the belt portion 45 and attaches to any one of loops 48 mounted on the outside of the other upper wing portion of the cover 41 to adjustably accommodate various body sizes.

Having now described several preferred embodiments of my invention, what is claimed is:

1. A reusable diaper set designed to conform to the body of a wearer, comprising:

an outer cover and an inner diaper pad;

said outer cover having an inside surface facing the wearer's body and an outside surface facing away from the wearer's body and consisting of an inner layer of moisture impervious material and an outer layer of decorative fabric, said outer cover having spaced apart, separate upper and lower wing portions connected by a central portion;

diaper fastening means mounted on the inside surface of said cover for securing a diaper pad thereto;

said inner diaper pad being contoured substantially to the entire shape of the outer cover and having fastening means for interlocking with the diaper fastening means on said outer cover to connect the diaper pad to the outer cover;

said diaper pad being constructed from layer of soft, water absorbent cotton fabric so that it can be washed when soiled and reused; and first fastening means for fastening the upper and lower wing portions together around the wearer's waist, and second fastening means including a belt secured to and extending from only one end of the upper wing portions, said belt having hook means attached to its terminal end for engaging any one of a plurality of loop connecting means horizontally disposed on the outside of the belt for adjustable engagement of the belt around the wearer's waist.

2. The diaper set of claim 1 wherein said diaper pad has a crotch portion with a pocket formed on either side thereof, said pocket having a layer of moisture impervious material inserted therein to provide a barrier against moisture escaping through the diaper pad.

3. The diaper set of claim 1 wherein the diaper fastening means consists of hook and loop fasteners with the respective mating portions mounted on the outer cover and diaper pad respectively.

4. The diaper set of claim 1 wherein the loop connecting means engaged by the hook means is a strip of loop fasteners secured to either the belt portion or the other end of the upper wing portions for adjustably mounting of the diaper set around the waist of the wearer.

5. A reusable diaper set designed to conform to the body of a wearer comprising:

an outer cover and an inner diaper pad, said outer cover having an inside surface facing the wearer's body and an outside surface facing away from the wearer's body and consisting of an inner layer of moisture impervious material and an outer layer of decorative fabric, said outer cover having spaced apart upper and lower wing portions connected by a central portion, said wing portions being provided with fastening means for fastening the wing portions together around the wearer's waist;

diaper fastening means mounted on the inside surface of said cover for securing a diaper pad thereto;

said inner diaper pad being contoured to the shape of the outer cover and having fastening means for interlocking with the diaper fastening means on said outer cover to connect the diaper pad to the outer cover;

said diaper pad being constructed from layers of soft, water absorbent cotton fabric; and a belt portion extending from one end of the upper wing portions, said belt portion having a hook means attached to its terminal end, loop means mounted on the outside of said belt portion, a belt loop mounted on the outside of the other end of the upper wing portions, said belt portion adapted to be inserted through said belt loop and then reversed upon itself to enable said hook to be attached to said loop means for fastening said upper wing portions around the waist of wearer.

6. A reusable diaper set designed to conform to the body of a wearer, comprising:

an outer cover and an inner diaper pad;

said outer cover having an inside surface facing the wearer's body and an outside surface facing away from the wearer's body and consisting of an inner layer of moisture impervious material and an outer layer of decorative fabric, said outer cover having spaced apart, separate upper and lower wing portions connected by a central portion;

diaper fastening means mounted on the inside surface of said cover for securing a diaper pad thereto;

said inner diaper pad being contoured substantially to the entire shape of the outer cover and having fastening means for interlocking with the diaper fastening means on said outer cover to connect the diaper pad to the outer cover;

said diaper pad being constructed from layer of soft, water absorbent cotton fabric so that it can be washed when soiled and reused;

hook means permanently attached to the end of each of said upper wing portions;

plurality of horizontally disposed loop connecting means mounted on the outside of and intermediate said lower wing portions, said hook means being adapted for connection to said loop connecting means for fastening the upper and lower wing portions around the waist of the wearer and a belt loop mounted on the outside surface at each end of said lower wing portions and adapted to receive a respective end of said upper wing portion therethrough prior to connecting said hook means to said loop connecting means.

* * * * *